United States Patent [19]

Saito et al.

[11] Patent Number: 5,021,191
[45] Date of Patent: Jun. 4, 1991

[54] OPTICALLY ACTIVE-2-ALKOXY-PROPYL ETHER AND LIQUID CRYSTAL COMPOSITION

[75] Inventors: Shinichi Saito; Makoto Ushioda; Hiromichi Inoue; Kazutoshi Miyazawa; Kouji Ohno, all of Kanagawa, Japan

[73] Assignee: Chisso Corporation, Ohsaka, Japan

[21] Appl. No.: 152,420

[22] Filed: Feb. 4, 1988

[30] Foreign Application Priority Data

Feb. 5, 1987 [JP] Japan .................................. 62-25235

[51] Int. Cl.$^5$ .................... C09K 19/34; C07D 241/10; C07D 239/24
[52] U.S. Cl. .......................... 252/299.61; 252/299.01; 252/299.6; 252/299.66
[58] Field of Search ............... 350/350 S; 252/299.01, 252/299.61, 299.66; 546/301, 302, 339

[56] References Cited

U.S. PATENT DOCUMENTS

| | | | |
|---|---|---|---|
| 4,556,727 | 12/1985 | Walba .............................. | 252/299.01 |
| 4,614,609 | 9/1986 | Inoue et al. ..................... | 252/299.66 |
| 4,676,925 | 6/1987 | Inoue et al. ..................... | 252/299.65 |
| 4,725,688 | 2/1988 | Zaguchi et al. ................. | 252/299.61 |
| 4,765,924 | 8/1988 | Inoue et al. ..................... | 252/299.61 |
| 4,775,223 | 10/1988 | Yoshinaga et al. ............ | 252/299.01 |
| 4,784,792 | 11/1988 | Inoue et al. ..................... | 252/299.61 |
| 4,834,904 | 5/1989 | Krause et al. ................... | 252/299.61 |

FOREIGN PATENT DOCUMENTS 3515373 11/1986 Fed. Rep. of Germany ........................ 252/299.61
63-51377 3/1988 Japan .............................. 252/299.61

Primary Examiner—John S. Maples
Assistant Examiner—Greg M. Sweet
Attorney, Agent, or Firm—Wenderoth, Lind & Ponack

[57] ABSTRACT

An optically active substance which, when added as a component of ferroelectric liquid crystal compositions, is extremely small in the reduction of the resulting liquid crystal temperature region, and a liquid crystal composition containing the same are provided, which substance is an optically active-2-alkoxy-propyl ether expressed by the formula (I)

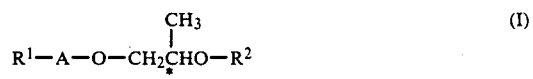

wherein $R^1$ represents a straight or branched chain alkyl, alkoxy, alkanoyl, alkanoyloxy or alkoxycarbonyl each of 1 to 18 C; $R^2$ represents a linear or branched chain alkyl each of 1 to 15 C; —A— represents a specified group constituted by two directly bonded, six-membered rings; and * indicates asymmetric carbon atom.

4 Claims, No Drawings

OPTICALLY ACTIVE-2-ALKOXY-PROPYL ETHER AND LIQUID CRYSTAL COMPOSITION

BACKGROUND OF THE INVENTION

1. Field of the Invention

This invention relates to a novel organic compound containing an optically active group and a liquid crystal composition containing the same. More particularly it relates to an organic compound useful as a component of ferroelectric liquid crystal compositions and a ferroelectric liquid crystal composition containing the same.

2. Description of the Prior Art

At present, TN (twisted nematic) type liquid crystal display mode has been most broadly employed as liquid crystal display elements This TN type liquid crystal display mode has many advantages of a low driving voltage, a small power consumption, etc. However, the mode is inferior in the aspect of the response rate to emissive type display elements such as electroluminescence, plasma display, etc. A new TN type display element having the twist angle changed to 180°–270° has also been developed, but it is still inferior in the aspect of the response time. As described above, efforts for various improvements have been made, but they have not yet been realized. However, in the case of a new display mode on which research has recently been earnestly advanced, there is a possibility of notably improving the response rate (Clark et al; Applied Phys. lett., 36, 899 (1980)). This mode is directed to a method utilizing chiral smectic phases such as chiral smectic C phase (hereinafter abbreviated to SC* phase) exhibiting ferroelectricity. Phases exhibiting ferroelectricity are not only SC* phase, but also phases of chiral smectic F, G, H, I, etc. have been known to exhibit ferroelectricity.

Many characteristics are required for practical use of ferroelectric liquid crystal materials in ferroelectric liquid crystal display elements, but at present, there is no single compound which satisfies such requirement. Thus, it is necessary to use a ferroelectric liquid crystal composition obtained by blending some liquid crystal compounds or non-liquid crystal compounds.

Until now, a number of ferroelectric liquid crystal compounds have been reported. Among these, a compound (hereinafter referred to as A) reported in U.S. Pat. No. 4,556,727, electric liquid crystal phases with a compound or composition exhibiting phases of achiral smectic C, F, G, H, I, etc. (hereinafter abbreviated to phases of SC phase, etc.) as a basic substance (Japanese patent application No. Sho 60-36003/1985). Further, it has also been reported that one or more compounds which are optically active but exhibit no ferroelectric liquid crystal phase are blended with a compound or composition exhibiting phases of SC, etc. as a basic substance to make up the whole into a ferroelectric liquid crystal composition (Mol. Cryst. Liq. Cryst. 89, 327 (1982)).

From the summary of the above facts, it is seen that when one or more optically active compounds, irrespective of whether or not they exhibit ferroelectric liquid crystal phases, are blended with a basic substance, it is possible to constitute a ferroelectric liquid crystal composition. Here, it has been known that the liquid crystalline physical properties of a basic substance have a great influence upon the physical properties of the resulting ferroelectric liquid crystal composition, and also the liquid crystal temperature range, viscosity, etc. of the basic substance have a direct influence upon the liquid crystal temperature range, response time, viscosity, tilt angle, etc. of the resulting ferroelectric liquid crystal composition.

Superior compounds as the above-mentioned basic substance include those containing a pyrimidine ring (Japanese patent application No. Sho 60-132817/1985), those containing a pyridine ring (Japanese patent application No. Sho 61-67961/1986), etc. and it appears that among these, those of directly bonded rings type having no bond group between the rings are particularly superior. Such compounds are also superior in that they have low viscosities and also exhibit phases of SC phase, etc. within a broad temperature range starting from low temperatures.

However, it has been found that when an optically active substance is added to the above-mentioned basic substances of directly bonded rings type to form a ferroelectric liquid crystal composition, there are those which are notably reduced in the ferroelectric liquid crystal temperature range by optically active substance. The optically active substance is preferred to be liquid crystals or substances having a constitution similar to those of liquid crystals, so to speak quasi liquid crystals, but it has been found that even if the optically active substance is liquid crystals or quasi liquid crystals, there

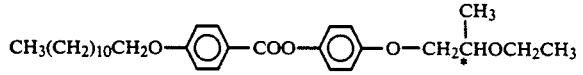

exhibits phase transition points of C.40.0° C. (SC*.35.0 ° C.) SA.46.8° C.I (C, SA and I being abbreviations of crystalline phase, smectic A phase and isotropic liquid phase, respectively), and its spontaneous polarization value (hereinafter abbreviated to Ps) is also as large as 15 (nC/cm$^2$); hence it is a very useful compound.

Further, another ferroelectric liquid crystal compound having the same 2-alkoxypropyl group as the optically active group of the compound A has also been reported in Japanese patent application laid-open No. Sho 61-112038/1986.

Still further, there have been reported not only ferroelectric liquid crystal compounds consisting only of ferroelectric liquid crystal compounds, but also ferroelectric liquid crystal compositions as a whole prepared by blending one or more compounds exhibiting ferroare substances which notably reduce the ferroelectric liquid crystal temperature range.

As will be described later in the Reference example, it has been found that when the compounds described above in U.S. Pat. No. 4,556,727 and Japanese patent application laid-open No. Sho 61-112038/1986 are added to a basic substance containing a pyridine ring or pyrimidine ring of directly bonded rings type, the ferroelectric liquid crystal temperature range is notably reduced or extinct and the Ps of the resulting composition is also far smaller than that expected from the addition proportion.

SUMMARY OF THE INVENTION

The object of the present invention is to provide an optically active substance which, when added as a component of ferroelectric liquid crystal compositions, is extremely small in the reduction of the resulting liquid crystal temperature region, and a liquid crystal composition containing the same.

The present invention resides in
an optically active-2-alkoxy-propyl ether expressed by the formula (I)

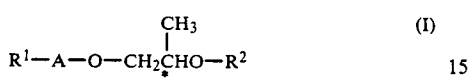

wherein $R^1$ represents a straight or branched chain alkyl group, alkoxy group, alkanoyl group, alkanoyloxy group or alkoxycarbonyl group each of 1 to 18 carbon atoms; $R^2$ represents a linear or branched chain alkyl group each of 1 to 15 carbon atoms; —A— represents

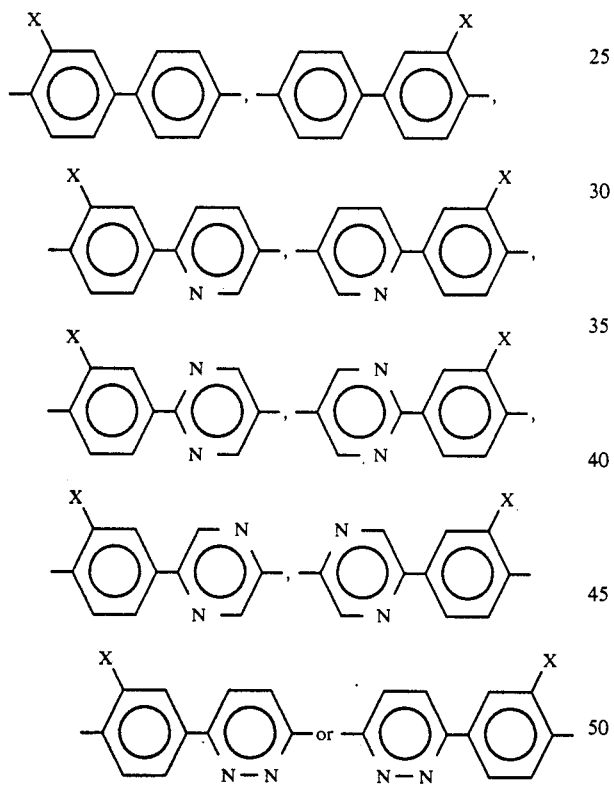

wherein X represents H, F, Cl, Br, Cn, $CH_3$ or $CH_3O$; and * indicates asymmetric carbon atom;
 a liquid crystal composition containing the above optically active-2-alkoxy-propyl ether, and
 a light switching element constituted by the above liquid crystal composition.

DETAILED DESCRIPTION OF PREFERRED EMBODIMENTS

In the formula (I), $R^1$ represents preferably a linear chain alkyl group or alkoxy group each of 4 to 14 carbon atoms, more preferably a linear chain alkyl group or alkoxy group each of 6 to 12 carbon atoms and $R^2$ represents preferably a linear or branched chain alkyl group each of 2 to 8 carbon atoms and in the case of branched chain alkyl group, it may be an optically active group.

Preferable concrete examples of —A— are as follows:

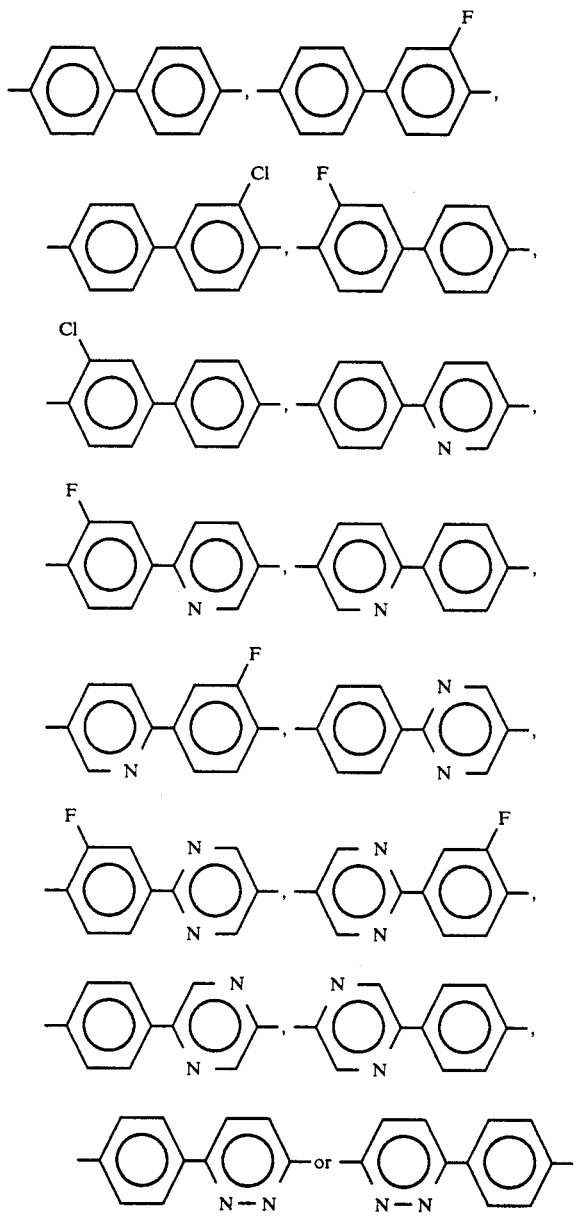

Representative examples of the compound of the formula (I) are as follows:
4'-hexyl-4-(2'-ethoxypropoxy)biphenyl
4'-hexyl-4-(2'-propoxypropoxy)biphenyl
4'-hexyl-4-(2'-butoxypropoxy)biphenyl
4'-hexyl-4-(2'-pentyloxypropoxy)biphenyl
4'-hexyl-4-(2'-hexyloxypropoxy)biphenyl
4'-hexyl-4-(2'-heptyloxypropoxy)biphenyl
4'-hexyl-4-(2'-octyloxypropoxy)biphenyl
4'-octyl-4-(2'-butoxypropoxy)biphenyl
 (Example 2, m.p. 33.0° C.)
4'-heptyloxy-4-(2'-ethoxypropoxy)biphenyl
4'-heptyloxy-4-(2'-butoxypropoxy)biphenyl
4'-heptyloxy-4-(2'-hexyloxypropoxy)biphenyl
4'-heptyloxy-4-(2'-octyloxypropoxy)biphenyl
4'-octyloxy-4-(2'-butoxypropoxy)biphenyl (Example 1, m.p. 74.5° C.)
4'-octyloxy-4-(2'-hexyloxypropoxy)biphenyl
  (Example 5, m.p. 68.3° C.)
4'-octyloxy-3-fluoro-4-(2'-methoxypropoxy)biphenyl
4'-octyloxy-3-fluoro-4-(2'-propoxypropoxy)biphenyl
4'-octyloxy-3-fluoro-4-(2'-pentyloxypropoxy)biphenyl
4'-octyloxy-3-fluoro-4-(2'-heptyloxypropoxy)biphenyl
4'-dodecyl-3-fluoro-4-(2'-hexyloxypropoxy)biphenyl
  (Example 8, m.p. 36.3° C.)
4'-nonyl-3-chloro-4(2'-ethoxypropoxy)biphenyl
4'-nonyl-3-chloro-4(2'-butoxypropoxy)biphenyl
4'-nonyl-3-chloro-4(2'-hexyloxypropoxy)biphenyl
4'-3-chloro-4-(2'-octyloxypropoxy)biphenyl
3'-fluoro-4'-decyloxy-4-(2'-methoxypropoxy)biphenyl
3'-fluoro-4'-decyloxy-4-(2'-propoxypropoxy)biphenyl
3'-fluoro-4'-decyloxy-4-(2'-pentyloxypropoxy)biphenyl
3'-fluoro-4'-decyloxy-4-(2'-heptyloxypropoxy)biphenyl
3'-chloro-4'-undecyloxy-4-(2'-ethoxypropoxy)biphenyl
3'-chloro-4'-undecyloxy-4-(2'-butoxypropoxy)biphenyl
3'-chloro-4'-undecyloxy-4-(2'-hexyloxypropoxy)biphenyl
3'-chloro-4'-undecyloxy-4-(2'-octyloxypropoxy)biphenyl
2-(4'-hexylphenyl)-5-(2'-methoxypropoxy)pyridine
2-(4'-hexylphenyl)-5-(2'-propoxypropoxy)pyridine
2-(4'-hexylphenyl)-5-(2'-pentyloxypropoxy)pyridine
2-(4'-hexylphenyl)-5-(2'-heptyloxypropoxy)pyridine
2-(3'-fluoro-4'-heptyloxyphenyl)-5-(2'-ethoxypropoxy)pyridine
2-(3'-fluoro-4'-heptyloxyphenyl)-5-(2'-butoxypropoxy)pyridine
2-(3'-fluoro-4'-heptyloxyphenyl)-5-(2'-hexyloxypropoxy)pyridine
2-(3'-fluoro-4'-heptyloxyphenyl)-5-(2'-octyloxypropoxy)pyridine
5-octyl-2-(4'-(2''-methoxypropoxy)phenyl)pyridine
5-octyl-2-(4'-(2''-propoxypropoxy)phenyl)pyridine
5-octyl-2-(4'-(2''-pentyloxypropoxy)phenyl)pyridine
5-octyl-2-(4'-(2''-hexyloxypropoxy)phenyl)pyridine
  (Example 4, m.p. 29° C.)
5-octyl-2-(4'-(2''-heptyloxypropoxy)phenyl)pyridine
5-heptyl-2-(4'-(2''-butoxypropoxy)phenyl)pyridine (Example 10, C $\xrightarrow{8.5° C.}$ SA $\xrightarrow{16.0° C.}$ I)

5-nonyl-2-(3'-fluoro-4'-(2''-ethoxypropoxy)phenyl)pyridine
5-nonyl-2-(3'-fluoro-4'-(2''-butoxypropoxy)phenyl)pyridine
5-nonyl-2-(3'-fluoro-4'-(2''-hexyloxypropoxy)phenyl)pyridine
5-nonyl-2-(3'-fluoro-4'-(2''-octyloxypropoxy)phenyl)pyridine
5-decyl-2-(3'-fluoro-(2''-hexyloxypropoxy)phenyl)pyridine
  (Example 7, m.p. 14.7° C.)
5-(2'-methoxypropoxy)-2-(4'-decyloxyphenyl)pyrimidine
5-(2'-propoxypropoxy)-2-(4'-decyloxyphenyl)pyrimidine
5-(2'-pentyloxypropoxy)-2-(4'-decyloxyphenyl)pyrimidine
5-(2'-heptyloxypropoxy)-2-(4'-decyloxyphenyl)pyrimidine
5-(2'-butoxypropoxy)-2-(4'-heptyloxyphenyl)pyrimidine
  (Example 9, m.p. 32.5° C.)
5-(2'-hexyloxypropoxy)-2-(4'-octyloxyphenyl)pyrimidine
  (Example 3, m.p. 32.5° C.)
5-(2'-ethoxypropoxy)-2-(3'-fluoro-4'-undecyloxyphenyl)pyrimidine
5-(2'-butoxypropoxy)-2-(3'-fluoro-4'-undecyloxyphenyl)pyrimidine
5-(2'-hexyloxypropoxy)-2-(3'-fluoro-4'-undecyloxyphenyl)pyrimidine
5-(2'-octyloxypropoxy)-2-(3'-fluoro-4'-undecyloxyphenyl)pyrimidine
5-octyl-2-(4'-(2''-ethoxypropoxy)phenyl)pyrimidine
5-octyl-2-(4'-(2''-butoxypropoxy)phenyl)pyrimidine
5-octyl-2-(4'-(2''-hexyloxypropoxy)phenyl)pyrimidine
5-octyl-2-(4'-(2''-octyloxypropoxy)phenyl)pyrimidine
5-dodecyl-2-(3'-fluoro-4'-(2''-methoxypropoxy)phenyl)pyrimidine
5-dodecyl-2-(3'-fluoro-4'-(2''-propoxypropoxy)phenyl)pyrimidine
5-dodecyl-2-(3'-fluoro-4'-(2''-pentyloxypropoxy)phenyl)pyrimidine
5-dodecyl-2-(3'-fluoro-4'-(2''-heptyloxypropoxy)phenyl)pyrimidine
5-heptyl-2-(3'-fluoro-4'-(2''-butoxypropoxy)phenyl)pyrimidine (Example 11) C $\xrightarrow{28.4° C.}$ I $\xrightarrow{0.7° C.}$ SA 5-heptyl-2-(3'-fluoro-4'-(2''-butoxypropoxy)phenyl)pyrimidine
  (Example 6, m.p. 21° C.)
2-(2'-ethoxypropoxy)-5- exyloxyphenyl)pyrazine
2-(2'-butoxypropoxy)-5-(4'-hexyloxyphenyl)pyrazine
2-(2'-hexyloxypropoxy)-5-(4'-hexyloxyphenyl)pyrazine
2-(2'-octyloxypropoxy)-5-(4'-hexyloxyphenyl)pyrazine
2-heptyl-5-(4'-(2''-methoxypropoxy)phenyl)pyrazine
2-heptyl-5-(4'-(2''-propoxypropoxy)phenyl)pyrazine
2-heptyl-5-(4'-(2''-pentyloxypropoxy)phenyl)pyrazine
2-heptyl-5-(4'-(2''-heptyloxypropoxy)phenyl)pyrazine
3-(2'-hexyloxypropoxy)-6-(4'-heptyloxyphenyl)pyridazine
  (Example 13, m.p. 68.0° C.)
3-(2'-ethoxypropoxy)-6-(4'-octyloxyphenyl)pyridazine
3-(2'-butoxypropoxy)-6-(4'-octyloxyphenyl)pyridazine
3-(2'-hexyloxypropoxy)-6-(4'-octyloxyphenyl)pyridazine
3-(2'-octyloxypropoxy)-6-(4'-octyloxyphenyl)pyridazine
3-(2'-hexyloxypropoxy)-6-(4'-nonylphenyl)pyridazine
  (Example 12, m.p. 64.2° C.)
3-nonyloxy-6-(4'-(2''-methoxypropoxy)phenyl)pyridazine
3-nonyloxy-6-(4'-(2''-propoxypropoxy)phenyl)pyridazine
3-nonyloxy-6-(4'-(2''-pentyloxypropoxy)phenyl)pyridazine
3-nonyloxy-6-(4'-(2''-heptyloxypropoxy)phenyl) pyridazine The compound of the formula (I) does not always exhibit liquid crystal phases by itself, but the compound has a structure similar to those of liquid crystals; hence when it is added to a basic substance, it does not notably reduce the resulting ferroelectric liquid crystal temperature range. This is evident from comparison of Example 4 with the Reference example. Further, as to the response time and Ps of these liquid crystal compositions, the composition containing the compound of the present invention is superior therein.

Further, when the compound of the present invention is used as a component of ferroelectric liquid crystal compositions, it is possible to increase the Ps thereof. In addition thereto, since the compound does not raise the viscosity of the compositions, the response rate increases. In other words, it can be said that the compound of the present invention itself has a low viscosity.

When the compound of the formula (I) of the present invention is added to a liquid crystal composition exhibiting achiral smectic C (Example 4), a ferroelectric liquid crystal composition having a large Ps is obtained, which exhibits a short response time and is a practical composition. Further, when the compound of the present invention is added to a liquid crystal composition exhibiting chiral smectic C phase but having a very small Ps, it is possible to raise the Ps of the composition up to a practical value. In short, the compound of the present invention is also important as a component bearing Ps of ferroelectric liquid crystal compositions.

Further, the compound of the formula (I) of the present invention has an optically active carbon atom; hence when it is added to a nematic liquid crystal, it has a capability of inducing a twisted structure (Example 3). Since nematic liquid crystals having a twisted structure, i.e. chiral nematic liquid crystals, form no reverse twist domain of TN type display elements, the compound of the present invention also has a function as an agent for preventing reverse twist domain from forming.

Further, the temperature dependency of the chiral pitch of chiral nematic liquid crystal compositions obtained by adding the compound of the present invention to nematic liquid crystal compositions are very flat as shown in Example 4. In the case of the chiral pitch of most of chiral substances currently used for addition to nematic liquid crystals, the higher the temperature, the longer the pitch, but such substances wherein the higher the temperature, the shorter the chiral pitch, have also been reported, and these substances reduce the temperature change in the threshold voltage of the electro-optical characteristics of TN type display elements (see 33rd Associated Lecture Meeting related to Applied Physics, Spring, 1986, Collected Preprints for Lecture, lp-G-7 (page 78)) and Japan Display, 86, Collected Preprints for Lecture, 8.3 (pages 286–289)). Since the compound of the present invention has physical properties similar to those of the above substances, it is possible for the compound to reduce the change in the threshold voltage by temperature, of the chiral nematic liquid crystals obtained by adding the compound.

Further, apart therefrom, in the case of the socalled super TN type display having the twist angle of TN type display changed to 180°-270°, the change of pitch by temperature notably reduced the display grade, whereas when a chiral nematic liquid crystal composition obtained by adding the compound of the present invention is used for the super TN type display, it is possible to prepare a superior super TN type display element the display grade of which is not damaged by the temperature change.

As described above, the compound of the present invention is also useful as a chiral component compound for chiral nematic compositions.

Further, most of generally used ferroelectric liquid crystal compositions exhibit a phase arrangement of Ne*, SA and SC* or Ne* and SC* in the order downward from the higher temperature side, since the presence of Ne* is required. The reason is that in order to improve the uniformity of display when the composition is made up into an element, it is necessary to arrange the molecules in Ne* phase, followed by cooling them to obtain a uniform molecular alignment in the SC* temperature range and as a result obtain a display element having no defect.

Here, the pitch length of Ne* phase becomes important, and for the above-mentioned purpose, it is required that the pitch length be a certain value or more and the values be nearly constant in Ne* temperature region. The reason is that unless the pitch length is constant, it is impossible to obtain a definite alignment due to temperature unevenness.

Since the compound of the present invention has an almost constant pitch length in the Ne* temperature region, it is a useful substance corresponding to the above-mentioned purpose.

Next, preparation of the compound of the formula (I) of the present invention will be described. The compound of the formula (I) may be prepared for example as follows:

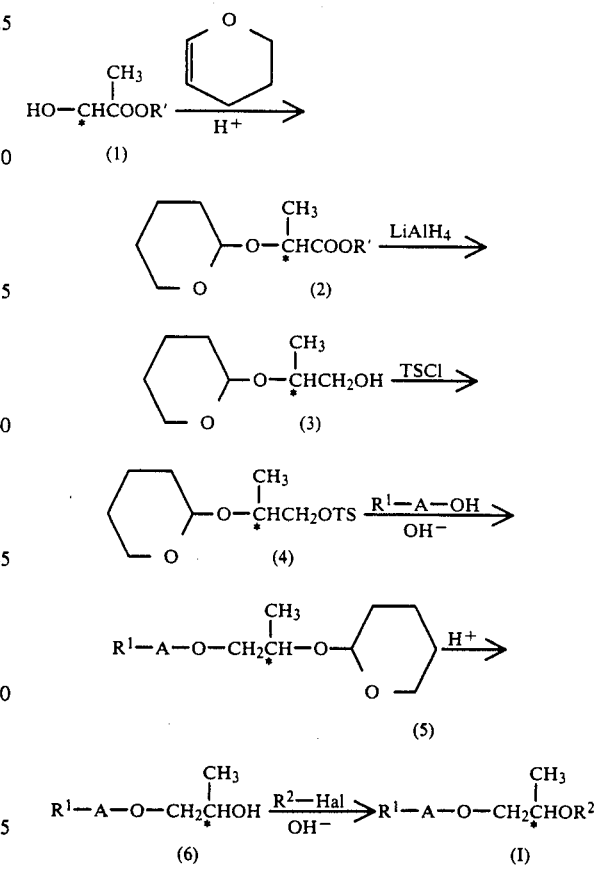

In the above formulas, TS represents p-toluenesulfonyl group; $R^1$ represents a short chain alkyl group such as methyl, ethyl, etc.; Hal represents a halogen atom; and $R^1$, $R^2$ and —A— are as defined above.

Namely, an alkyl lactate (1) is reacted with 2,3-dihydropyrane to obtain an alkyl 2-tetrahydropyranyloxypropionate (2), which is reduced with a reducing agent such as $LiAlH_4$ into an alcohol (3), which is tosylated with p-toluenesulfonyl chloride to obtain a compound (4), which is etherified to obtain a compound (5), which is treated with an acid to obtain an alcohol (6), which i etherified to obtian a desired compound of the formula (I).

As to the lactic acid ester as the starting raw material, its S-form and R-form are both commercially available; hence both the enantiomers of the formula (I) may be optionally prepared.

Beside the above preparation, the compound of the formula (I) may also be prepared through the following passageway:

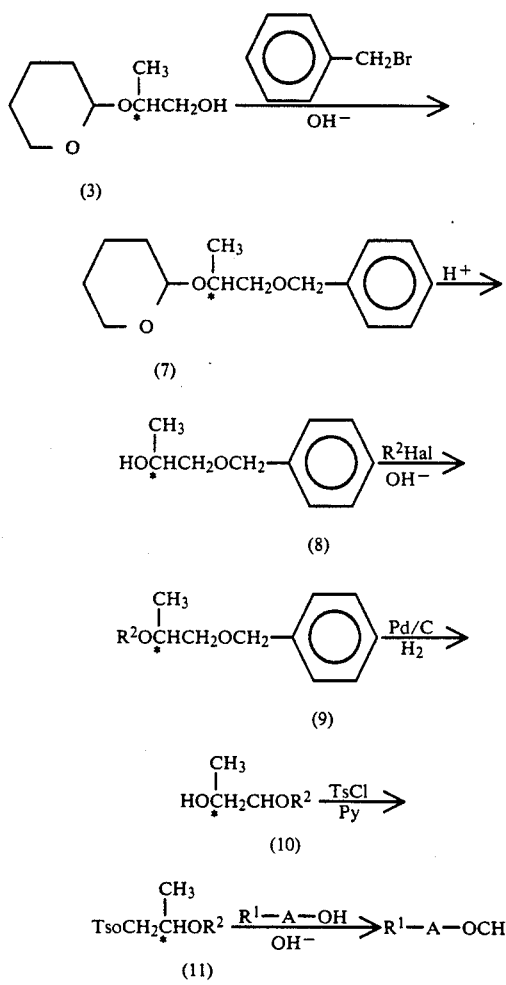

Namely, an alcohol (3) is benzyletherified to obtain a compound (7), which is treated with an acid to obtain an alcohol (8), which is freed and etherified to obtain a compound (9), which is subjected to hydrogenolysis to obtain an alcohol (10), which is tosylated to obtain a compound (11), which is etherified to obtain the compound of the formula (I).

Further, the compound of the formula (I) may also be prepared through the following passageway:

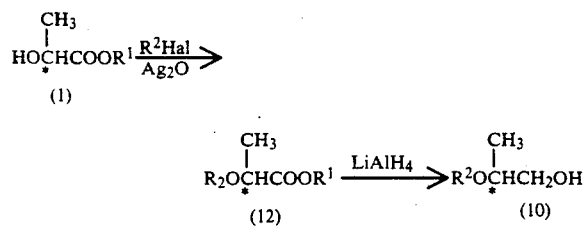

Namely, an alkyl lactate (1) is etherified with silver oxide to obtain a compound (12), which is reduced to obtain an alcohol (10), which is treated as above to obtain the compound of the formula (I).

The compound and liquid crystal composition of the present invention will be described in more detail by way of Examples.

EXAMPLE 1

Preparation of S-4'-octyloxy-4-(2'-butoxy-propoxy)-biphenyl (a compound of the formula (I) wherein $R^1$ represents octyloxy, $R^2$ represents butyl and —A— represents

)

(1) A mixture of (2S)-2-tetrahydropyranyloxy-1-hydroxypropane (137 g, 0.85 mol) prepared according to the method described in a literature (C. Malanga et al, Synthetic Communications, 12 (1), 67–70 (1982)) with anhydrous pyridine (600 g) was cooled with ice, followed by dropwise adding to the mixture, a solution of p-toluenesulfonyl chloride (165 g, 0.87 mol) in pyridine (200 ml), agitating the mixture at 0° C. for 2 hours, successively agitating it at room temperature for 2 hours, allowing it to stand overnight, adding toluene (1 l), further adding 2N-NaOH solution (500 ml), separating the resulting organic layer, several times washing it with water until the washing water became neutral, drying it with $MgSO_4$, and distilling off the solvent to obtain (2 S)2-(2'-tetrahydropyranyloxy)-1-(p-toluenesulfonyloxy)-propane (257 g) (yield 95.9%).

A solution of (2 S)2-(2'-tetrahydropyranyloxy)-1-(p-toluenesulfonyloxy)propane (20 g) in N,N-dimethylformamide (hereinafter abbreviated to DMF) (300 ml) was added to a mixture of sodium hydrode (60%) (2 g), 4-hydroxy-4'-octyloxy-biphenyl (10 g) and tetrahydrofuran (hereinafter abbreviated to THF) (200 ml), followed by agitating the mixture at 60° C. for 4 hours, allowing it to cool down to room temperature, adding toluene (300 ml) and water (300 ml), separating the resulting organic layer, washing it with an alkali and then with water, concentrating, adding to the resulting concentrate, ethanol (300 ml) and pyridium-p-toluenesulfonate (hereinafter abbreviated to PPTS) (2 g), agitating the mixture at 50° C. for 3 hours, distilling off ethanol, adding toluene (300 ml), washing the resulting organic layer with water, concentrating it phenyloxy)-propan-2-ol (8 g) (m.p. 138.5°–140.3° C.). (2) DMF (40 ml) was added to sodium hydride (60%) (0.6 g), followed by adding S-1-(4'-octyloxy-4-biphenylyloxy)-propan-2-ol (2 g) obtained in the above (1), further, adding butyl bromide (1.2 g), agitating the mixture at room temperature for 12 hours, adding water (200 ml) to the resulting reaction liquid, extracting with toluene (150 ml), washing the resulting organic layer with an acid, then with an alkali and further with water, concentrating it, purifying according to column chromatography using a column having activated alumina filled therein, and recrystallizing from ethanol to obtain the captioned compound, S-4'-octyloxy-4(2'-butoxy-propoxy)-biphenyl (1.4 g) (m.p. 74.5° C.).

EXAMPLE 2

Preparation of S-4'-octyl-4-(2'-butoxy-propoxy)-biphenyl (a compound of the formula (I) wherein $R^1$ represents octyl, $R^2$ represents butyl and —A— represents

)

Reaction and purification were carried out according to the process of Example 1-(1), using 4-hydroxy-4'-octylbiphenyl in place of 4-hydroxy-4'-octyloxy-biphenyl in Example 1-(1), to obtain S-1-(4'-octyl-4-biphenylyloxy)propan-2-ol, which was subjected to reaction and purification according to Example 1-(2) to obtain S-4'-octyl-4-(2'-butoxy-propoxy)-biphenyl (m.p. 33° C.).

EXAMPLE 3

Preparation of R-5-(2'-hexyloxypropyloxy)-2-(4'-octyloxyphenyl)pyrimidine (a compound of the formula (I) wherein $R^1$ represents octyloxy, $R^2$ represents hexyl and —A— represents

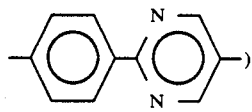)

(1) (2R)-2-tetrahydropyranyloxy-1-hydroxypropane (60 g, 0.37 mol) was dropwise added to a suspension of sodium hydride (60%) (22 g) in THF (100 ml) under ice cooling. After completion of the dropwise addition, a solution of benzyl bromide (70 g) in DMF (300 ml) was dropwise added, followed by agitating the mixture at room temperature for 6 hours, pouring it into water (500 ml), extracting with toluene (300 ml), washing the resulting organic layer with water, concentrating it, dissolving the concentrate in ethanol (300 ml), adding 6N-hydrochloric acid (20 ml), agitating the mixture at 20° C. for 2 hours, distilling off ethanol, adding toluene (300 ml), washing the resulting organic layer with an alkali and then with water and distilling it under reduced pressure to obtain (R)-1-benzyloxy-2-propanol (b.p. 105°–107° C./5 mmHg) (28 g).

(R)-1-benzyloxy-2-propanol (25 g, 0.15 mol) obtained above was dropwise added to a suspension of sodium hydride (60%) (10 g) in THF (50 ml), followed by dropwise adding to the mixture, a solution of hexyl bromide (31 g, 0.19 mol) in DMF (200 ml), agitating the mixture at room temperature for 6 hours, adding water (500 ml), extracting the mixture with toluene (300 ml), washing the resulting organic layer with an acid, then with an alkali and further with water, concentrating, and distilling the concentrate under reduced pressure to obtain (R)-1-benzyloxy-2-hexyloxypropane (b.p. 145°–150° C./5 mmHg) (25 g).

A mixture liquid of the above (R)-1-benzyloxy-2-hexyloxy-propane (25 g), palladium/carbon catalyst (2.0 g) and ethanol (200 ml) was subjected to hydrogenolysis. After completion of the reaction, the catalyst was filtered off, followed by concentrating the mother liquor, and distilling the concentrate under reduced pressure to obtain (R)-2-hexyloxy-1-propanol (b.p. 67°–68° C./4 mmHg) (11.6 g).

(2) A solution of p-toluenesulfonyl chloride (15 g, 79 mmols) in pyridine (100 ml) was dropwise added to a solution of the above (R)-2-hexyloxy-1-propanol (10 g, 12 mmols) in pyridine (200 ml) under ice cooling, followed by agitating the mixture under ice cooling for one hour, successively agitating it at room temperature for 6 hours, adding toluene (300 ml) and cold water (300 ml), washing the resulting organic layer with an acid, then with an alkali and further with water and concentrating it to obtain (R-1-(p-toluenesulfonyloxy)-2-hexyloxy-propane (23.4 g).

(3) A solution of 5-hydroxy-2-(4'-octyloxyphenyl)-pyrimidine (1.0 g) in THF (30 ml) was dropwise added to a suspension of sodium hydride (60%) (0.25 g) in THF (30 ml), followed by further adding a solution of the above (R)-1-(p-toluenesulfonyloxy)-2-hexyloxypropane (1.6 g) in DMF (50 ml), agitating the mixture at about 60° C. for 4 hours, adding water (200 ml) and toluene (200 ml), separating the resulting organic layer, washing it with an alkali, then with an acid and further with water, concentrating it, purifying the resulting concentrate according to column chromatography using a column having activated alumina filled therein and using toluene as an eluent, and recrystallizing from ethanol to obtain R-5-(2'-hexyloxypropyloxy)-2(4'-octyloxyphenyl)pyrimidine (m.p. 32.2° C.) (1.0 g).

EXAMPLE 4

Preparation of R-5-octyl-2-(4'-(2''-hexyloxypropoxy)phenyl)pyridine (A compound of the formula (I) wherein $R^1$ represents octyl, $R^2$ represents hexyl and —A— represents

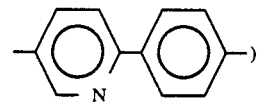)

Reaction and purification were carried out according to the process of Example 3-(3), using sodium hydride (60%) (0.25 g), 5-octyl-2-(4'-hydroxyphenyl)pyridine (1.0 g) and (R)-1-(p-toluenesulfonyloxy)-2-hexyloxypropane (1.6 g) obtained in Example 3-(2), to obtain R-5-octyl-2-(4'-(2''-hexyloxypropoxy)phenyl)pyridine (m.p. 29.0° C.) (0.7g).

EXAMPLE 5

Preparation of R-4'-octyloxy-4-(2'-hexyloxypropoxy)-biphenyl (a compound of the formula (I) wherein $R^1$ represents octyloxy, $R^2$ represents hexyl and —A— represents

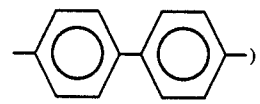)

Reaction and purification were carried out according to the process of Example 4, using 4'-octyloxy-4-hydroxy-biphenyl in place of 5-octyl-2-(4'-hydroxyphenyl)pyridine in Example 4 to obtain R-4'-octyloxy-4-(2'-hexyloxypropoxy)-biphenyl (m.p. 68.3° C.) (1.1 g).

EXAMPLE 6

Preparation of R-5-heptyl-2-(3'-fluoro-4'-(2"-hexyloxypropoxy)pyrimidine (a compound of the formula (I) wherein $R^1$ represents heptyl, $R^2$ represents hexyl and —A— represents

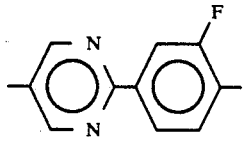

Reaction and purification were carried out according to the process of Example 4, using 5-heptyl-2-(3'-fluoro-4'-hydroxyphenyl)pyrimidine in place of 5-octyl-2(4'-hydroxyphenyl)pyridine in Example 4, to obtain R-5-heptyl-2-(3'-fluoro-4'-(2"-hexyloxypropoxy))pyrimidine (m.p. 21° C.) (0.5 g).

EXAMPLE 7

Preparation of R-5-decyl-2-(3'-fluoro-4'-(2"-hexyloxypropoxy)phenyl)pyridine (a compound of the formula (I) wherein $R^1$ represents decyl, $R^2$ represents hexyl and —A— represents

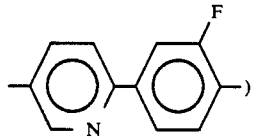

Reaction and purification were carried out according to the process of Example 4, using 5-decyl-2-(3'-fluoro4'-hydroxypehnyl)pyridine in place of 5-octyl-2-(4'-hydroxyphenyl)pyridine in Example 4, to obtain R-5-decyl-2-(3'-fluoro-4'-(2"-hexyloxypropoxy)-phenyl)pyridine (m.p. 14.7° C.) (0.5 g).

EXAMPLE 8

Preparation of R-4'-dodecyl-3-fluoro-4-(2"-hexyloxypropoxy)biphenyl (a compound of the formula (I) wherein $R^1$ represents dodecyl, $R^2$ represents hexyl and —A— represents

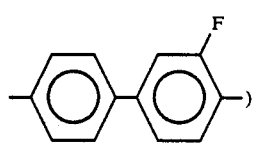

Reaction and purification were carried out according to the process of Example 4, using 4'-dodecyl-3-fluoro-4-hydroxy-biphenyl in place of 5-octyl-2-(4'-hydroxyphenyl)pyridine, to obtain R-4'-dodecyl-3-fluoro-4-(2"-hexyloxypropoxy)biphenyl (m.p. 36.3° C.) (0.7 g).

EXAMPLE 9

Preparation of R-5-(2'-butoxypropoxy)-2-(4'-heptyloxyphenyl)pyrimidine (a compound of the formula (I) wherein $R^1$ represents heptyloxy, $R^2$ represents butyl and —A— represents

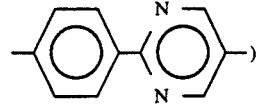

(1) A mixture liquid methyl R-lactate (156.2 g), butyl iodide (386.4 g), 18-crown-6(1, 4, 7, 10, 13, 16-hexaoxycyclooctadecane) (5.4 g) and silver oxide (312.9 g) was agitated at room temperature for 48 hours. After the reaction, solids were filtered off, followed by washing the solids with toluene (300 ml), combining resulting solutions, washing the solution with water, concentrating it and distilling the concentrate under reduced pressure to obtain (R)-methyl 2-butoxypropionate (b.p. 90°-91° C./38 mmHg) (104 g).

(2) THF (200 ml) was added to $LiAlH_4$ (16.8 g), followed by agitating the mixture under ice cooling, dropwise adding thereto a solution of (R)-methyl 2-butoxypropionate (54 g) in THF (150 ml), agitating the mixture at room temperature for 3 hours, again cooling it with ice, adding water, extracting with heptane (300 ml) water-washing, concentrating and distilling the resulting concentrate under reduced pressure to obtain (R)-2-butoxy-1-propanol (29.3 g).

(3) Reaction and purification were carried out according to the process of Example 3-(2), using (R)-2-butoxy-1propanol,(18 g), p-toluenesulfonyl chloride (28 g) and pyridine, to obtain (R)-1-(p-toluenesulfonyloxy)-2-butoxy-propane (31 g).

(4) Reaction and purification were carried out according to the process of Example 3-(3), using 5-hydroxy-2-(4'-heptyloxyphenyl)pyrimidine (1.0 g) and (R)-1-(p-toluenesulfonyloxy)-2-butoxy-propane (1.5 g), to obtain R-5-(2'-butoxypropoxy)-2-(4'-heptyloxyphenyl)pyrimidine (m.p. 32.5° C.) (0.5 g).

EXAMPLE 10

Preparation of R-5-heptyl-2-(4'-(2"-butoxypropoxy)-phenyl)pyridine (a compound of the formula (I) wherein $R^1$ represents heptyl, $R^2$ represents butyl and —A— represents

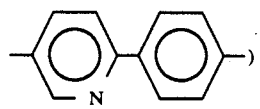

Reaction and purification were carried out according to the process of Example 9-(4), using 5-heptyl-2(4'-hydroxyphenyl)pyridine in place of 5-hydroxy-2(4'-heptyloxyphenyl)pyrimidine in Example 9-(4), to obtain R-5-heptyl-2-(4'-(2"-butoxypropoxy)phenyl)pyridine (0.6 g).

This product exhibited phase transition points of

EXAMPLE 11

Preparation of R-5-heptyl-2-(3'-fluoro-4'-(2"-butoxypropoxy)phenyl)pyrimidine (a compound of the formula (I) wherein $R^1$ represents heptyl, $R^2$ represents butyl and —A— represents

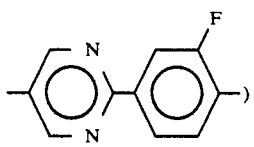

Reaction and purification were carried out according to the process of Example 9-(4), using 5-heptyl-2-(3'-fluoro-4'-hydroxyphenyl)pyrimidine in place of 5-hydroxy-2-(4'-heptyloxyphenyl)pyrimidine, to obtain R-5-heptyl-2-(3'-fluoro-4'-(2''-butoxypropoxy)phenyl)-pyrimidine (0.6 g).

This product exhibited phase transition points of

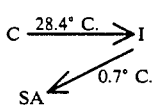

EXAMPLE 12

Preparation of R-3-(2'-hexyloxypropoxy)-6-(4'-nonylphenyl)pyridazine
  (a compound of the formula (I) wherein $R^1$ represents nonyl, $R^2$ represents hexyl and —A— represents

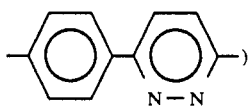

Toluene (20 ml) and (R)-2-hexyloxy-1-propanol (1 g) obtained in Example 3-(1) were added to sodium hydride (55%, oily) (0.4 g), followed by adding 3-chloro-6-(4'-nonylphenyl)pyridazine (1.4 g) and toluene (30 ml), heating the mixture under reflux for 6 hours, adding water (100 ml), separating the resulting organic layer, purifying it according to column chromatography using activated alumina filled therein and recrystallizing from ethanol to obtain R-3-(2'-hexyloxypropoxy)-6(4'-nonylphenyl)pyridazine (m.p. 56.7° C.) (0.8 g).

EXAMPLE 13

Preparation of R-3-(2'-hexyloxypropoxy)-6-(4'-heptyloxyphenyl)pyridazine
  (a compound of the formula (I) wherein $R^1$ represents a heptyloxy, $R^2$ represents hexyl and —A— represents

Using 3-chloro-6-(4'-heptyloxyphenyl)pyridazine in place of 3-chloro-6-(4'-nonylphenyl)pyridazine in Example 12, R-3-(2'-hexyloxypropoxy)-6-(4'-heptyloxyphenyl)pyridazine (m.p. 61.5° C.) (0.6 g).

EXAMPLE 14

A nematic liquid crystal composition consisting of

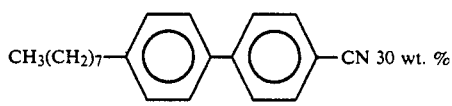

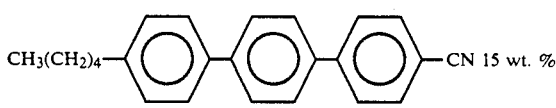

was filled in a cell provided with transparent electrodes each obtained by coating polyvinyl alcohol (PVA) as an agent for aligning treatment onto the surface and rubbing the resulting surface to subject it to a parallel aligning treatment and having a distance between the electrodes of 10 μm to prepare a TN type display cell, which was observed under a polarizing microscope. As a result, formation of reverse twist domain was observed. To this nematic liquid crystal composition was added the compound of Example 1 in an amount of 0.5% by weight, and a TN type cell was similarly prepared and observed. As a result, no reverse twist domain was formed and a uniform nematic phase was observed.

EXAMPLE 15 (USE EXAMPLE 1)

A chiral nematic liquid crystal composition obtained by adding the compound of Example 1 in an amount of 1% by weight to ZLI-1132 manufactured by Merck Company was subjected to measurement of its chiral pitch according to Cano-Wedge method (see Applied Physics, 43 (2), 126–131 (1974)). The results were as follows:

| Temperature (°C.) | Pitch (μm) |
| --- | --- |
| 20 | 17.4 |
| 30 | 17.5 |
| 40 | 17.5 |
| 50 | 17.5 |
| 60 | 17.4 |

EXAMPLE 16 (USE EXAMPLE 2)

A liquid crystal composition (B) consisting of

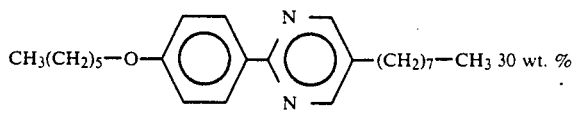

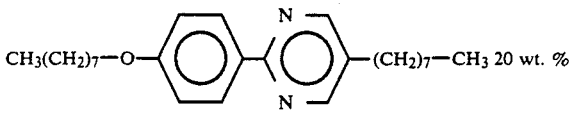 20 wt. %

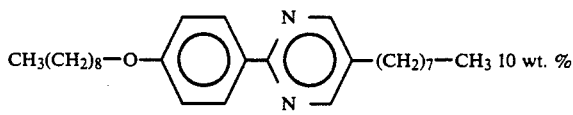 10 wt. %

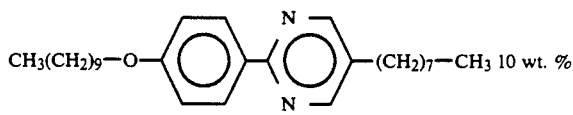 10 wt. %

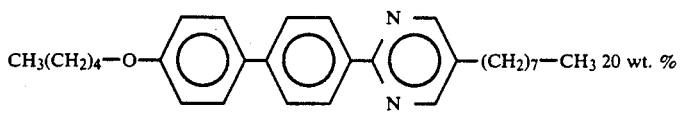 20 wt. %

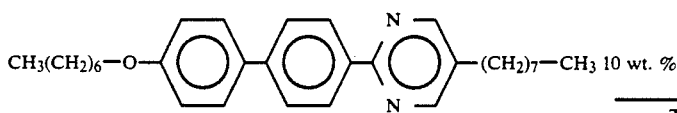 10 wt. % exhibits phase transition points of C→SC 4° C., SC→SA 65° C., SA→N 79° C. and N→I 90° C. wherein SC and N are abbreviations of smectic C phase and nematic phase, respectively. Further, since this composition (B) consists only of non-optically active compounds, it is not a chiral liquid crystal and hence not a ferroelectric liquid crystal and thus exhibits no spontaneous polarization.

A mixture of this composition (B) (80% by weight) with the compound of Example 1 of the present invention, i.e. a composition (C), exhibited phase transition points of SC*→SA 57° C., SA→N* 69° C. and N*→I 78° C.

(wherein N* is an abbreviation of chiral nematic phase), although the phase transition point of C→SC* was unclear. This composition (C) was filled in a cell of 2 μm thickness provided with transparent electrodes each obtained by coating PVA as an agent for aligning treatment and rubbing the resulting surface to subject it to a parallel aligning treatment. The resulting element was placed between two sheets of crossed polarizers and an electric field was impressed. The response time was sought from change in the intensity of transmitted light by impressing ±10 V, and Ps was sought according to Sowyer-Tower method. The results were as follows:

| Temperature (°C.) | Response time (μsec) | Ps (nC/cm²) |
|---|---|---|
| 50 | 90 | 2.3 |
| 40 | 120 | 2.8 |
| 30 | 160 | 3.3 |

REFERENCE EXAMPLE

With the compound (A) reported in the abovementioned U.S. Pat. No. 4,556,727, the response rate and Ps were sought under the same conditions as in Example 4. The results were as follows:

| Temperature (°C.) | Response time (μsec) | Ps (nC/cm²) |
|---|---|---|
| 30 | 180 | 9.0 |
| 25 | 250 | 12.3 |

Further, a mixture of the above composition (B) (80% by weight) with the compound (A) (20% by weight), i.e. a composition (D), exhibited phase transition points of SC*→SA 30° C., SA→Ne* 79° C. and Ne*→I 81° C.

With this composition (D), the response time and Ps were sought. However, although the electric field inversion behavior was observed, the response time was as extremely long as 1 msec or more, and Ps was also as extremely small as 0.5 (nC/cm²) or less.

What we claim is:

1. An optically active-2-alkoxy-propyl ether expressed by the formula (I)

wherein R¹ represents a straight chain alkyl group, of 6 to 12 carbon atoms; R² represents a linear chain alkyl group of 2 to 8 carbon atoms; —A— represents

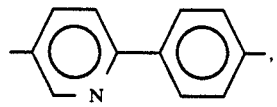

and * indicates an asymmetric carbon atom.

2. A liquid crystal composition comprising at least two components at least oen of which is an optically active-2-alkoxy-propyl ether expressed by the formula (I) as set forth in claim 1.

3. A liquid crystal composition according to claim 2, exhibiting a chiral nematic liquid crystal phase.

4. A liquid crystal composition according to claim 2, exhibiting a chiral smectic liquid crystal phase.

* * * * *